United States Patent [19]

Matsumura et al.

[11] 4,372,655

[45] Feb. 8, 1983

[54] AUTOMATIC EYE-REFRACTOMETER

[75] Inventors: Isao Matsumura, Yokosuka; Yasuyuki Ishikawa, Kawaguchi; Shigeo Maruyama, Kawasaki; Reiji Hirano; Yoshimi Kohayakawa, both of Yokohama, all of Japan

[73] Assignee: Canon Kabushiki Kaisha, Tokyo, Japan

[21] Appl. No.: 75,115

[22] Filed: Sep. 13, 1979

[30] Foreign Application Priority Data

Sep. 20, 1978 [JP] Japan .............................. 53-115647

[51] Int. Cl.$^3$ ........................... A61B 3/14; A61B 3/10
[52] U.S. Cl. .................................... 351/206; 351/211; 351/237
[58] Field of Search ...................... 351/6, 7, 9, 13, 39

[56] References Cited

U.S. PATENT DOCUMENTS 3,802,768  4/1974  Robinson et al. ..................... 351/39
3,883,233  5/1975  Guilino ............................. 351/13 X
3,915,564 10/1975  Urban ................................ 351/7
4,021,102  5/1977  Iizuka .............................. 351/6 X Primary Examiner—John K. Corbin
Assistant Examiner—Rodney Bovernick Attorney, Agent, or Firm—Fitzpatrick, Cella, Harper & Scinto

[57] ABSTRACT

An automatic eye-refractometer includes a projector for projecting a test pattern onto the fundus of an eye to be examined, a photo-electric device disposed to receive an image of the test pattern reflected upon the fundus of the eye, a calculator for calculating the refractive power of the eye using outputs from the photo-electric device and a processor for processing the results of the calculation into digital video signals. The eye-refractometer is further provided with a video camera for image picking up the front part of the eye through an objective lens of the projector to produce video signals and a video display device for displaying on a screen a picture produced from the video signals. With the measuring apparatus, the examiner can observe the image of the front part of the eye to be examined and can properly arrange the eye and the objective lens to each other while watching the picture displayed on the screen. By putting the digital signals into the video display device from the processor there are also displayed on the screen numerals, characters or other symbols informing of the refractive power of the examined eye.

7 Claims, 18 Drawing Figures

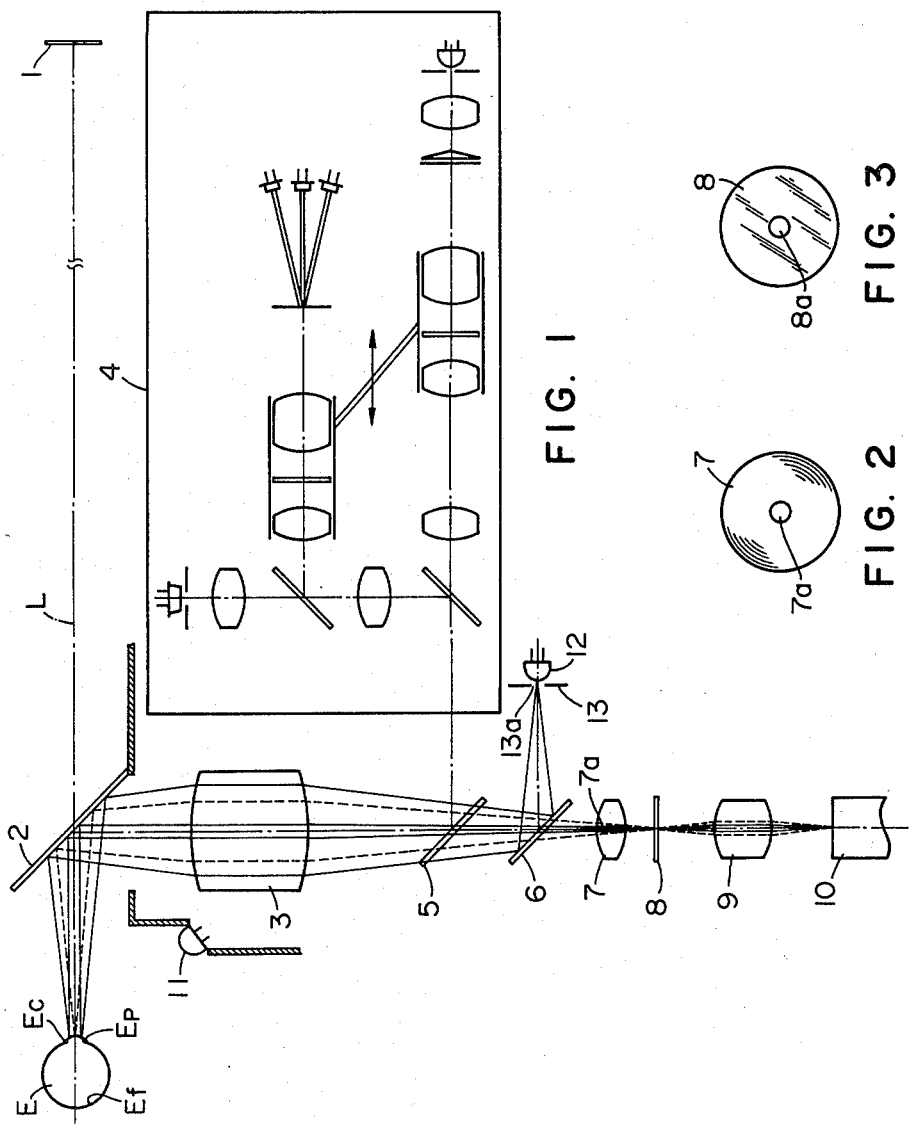
FIG. 1
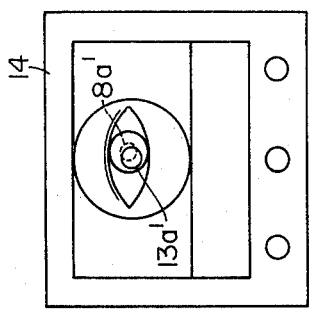
FIG. 4
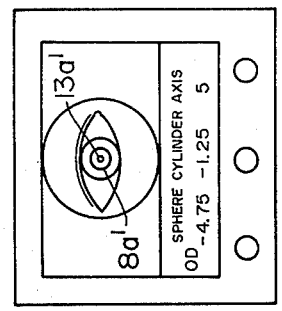
FIG. 5
FIG. 2
FIG. 3

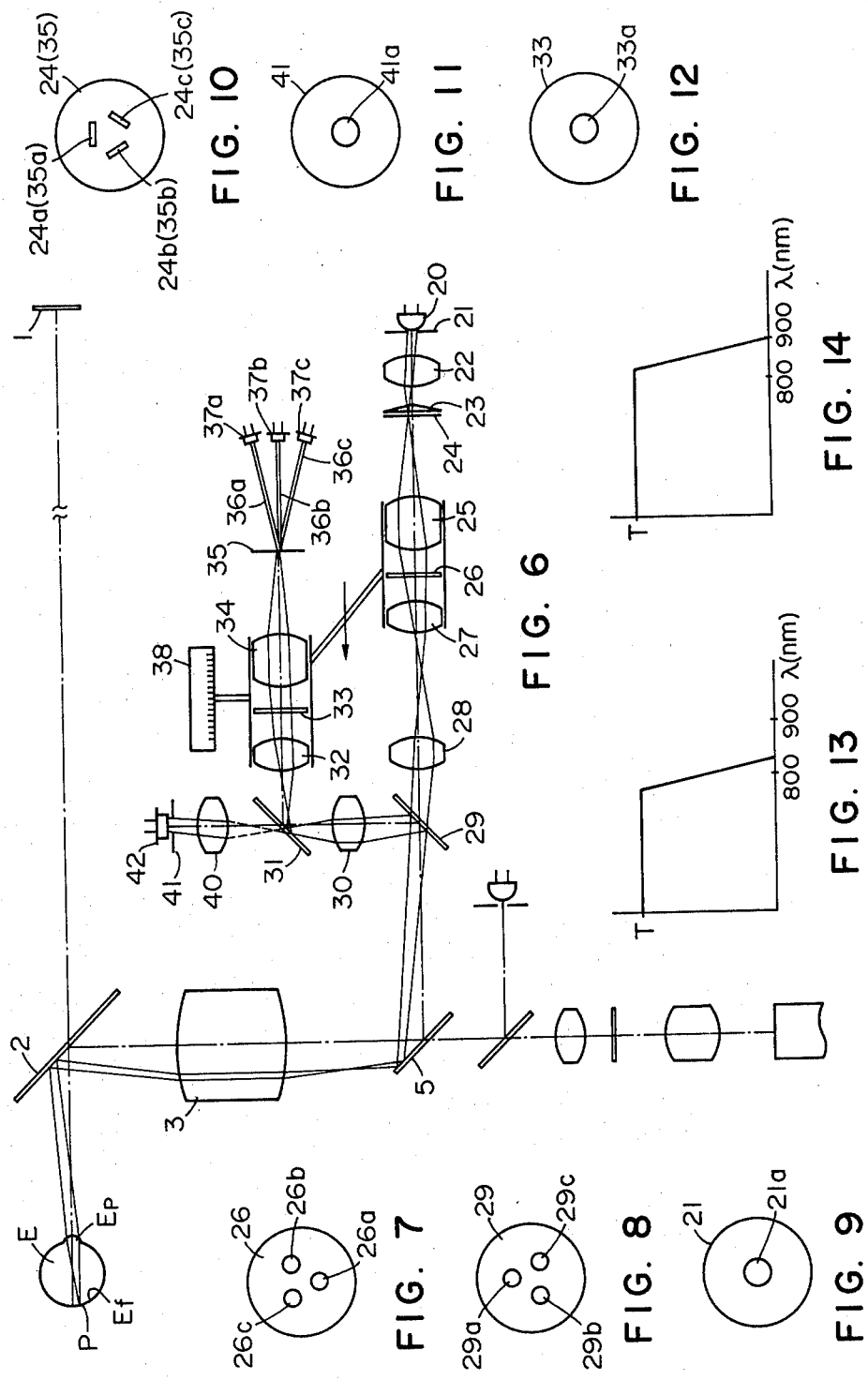

AUTOMATIC EYE-REFRACTOMETER

BACKGROUND OF THE INVENTION

1. Field of the Invention

The present invention relates to an apparatus for measuring the refractive power of eye and more particularly to such apparatus for refractometry which is able to automatically measure information of eye refractive power including information of astigmatism and which has a video display device to display the measured information in terms of numerals, characters or other symbols.

2. Description of the Prior Art

Eye-refractometers have been used for a long time to examine human eyes and more practically to obtain data for adjustment of spectacles. For this purpose there have been known and proposed various types of eye-refractometers in view of structure and function.

As well known to those skilled in the art, to determine eye refractive power it is required to measure three values, that is, spherical diopter, astigmatism and astigmatic axis. Spherical diopter is diopter in the longitudinal axis in which the diopter is maximum. Astigmatism is changed of diopter with change of the longitudinal direction and astigmatic axis is the longitudinal direction in which diopter is maximum.

In some known eye-refractometers, for example, in those disclosed in U.S. Pat. Nos. 3,883,233 and 3,888,569, the whole optical system or a portion thereof is rotated about its optical axis so that the measuring direction along the longitudinal direction may be changed so as to enable a continuous measurement of eye refractive power along the longitudinal direction.

Also, we, the inventors of the present invention already proposed a novel eye-refractometer in our prior application, U.S. Ser. No. 944,304, now U.S. Pat. No. 4,293,198.

For eye-refractometry it is essential to establish proper alignment of the refractometer to the eye to be examined and to make a correct adjustment of the spacing therebetween. Effective methods for carrying out the necessary adjustment have been proposed in U.S. Pat. Nos. 3,871,772 and 3,864,030 as well as in U.S. Ser. No. 832,829 applied by the same assignee as the present application.

It is also essential to exclude the adverse effect of wink of the eyes on the measurement. If a person under measurement winks his eyes, then it will produce a false result of measurement. For this reason, the above mentioned U.S. Pat. No. 3,888,569 proposed a measuring apparatus in which measurement is stopped during winking of the subject eye. Also, in U.S. Pat. No. 4,149,787 assigned to the assignee of the present application, there has been proposed an eye examining apparatus suitable for detection of winking during measurement.

SUMMARY OF THE INVENTION

Accordingly, it is an object of the present invention to provide an eye-refractometer which is good in operability and high in measurement accuracy.

It is another object of the invention to provide an eye-refractometer which makes it possible to determine whether or not a person under measurement is correctly gazing at a fixation object.

It is a further object of the invention to provide such eye-refractometer in which the results of measurement are digitally displayed on a screen of video display device.

It is still a further object of the invention to provide such refractometry apparatus which is able to display not only the results of measurement but also an image of the eye to be measured on a central monitoring screen.

It is another object of the invention to provide an eye-refractometer by which it is easy to arrange the measuring system and the eye to be measured properly.

It is a further object of the invention to provide such eye-refractometer which permits detection of variation of quantity of light from the eye under measurement.

It is still a further object of the invention to provide such eye-refractometer in which any winking of the tested eye during measurement can be displayed to fall under the examiner's observation.

Other and further objects, features and advantages of the invention will appear more fully from the following description taken in connection with the accompanying drawings.

BRIEF DESCRIPTION OF THE DRAWINGS

FIG. 1 is a schematic sectional view of an embodiment of the present invention;

FIGS. 2 and 3 are plan views of one structural component of the embodiment;

FIGS. 4 and 5 are front views of the image receiving device used in the embodiment;

FIG. 6 shows the embodiment in the same view as FIG. 1;

FIGS. 7 to 12 are plan views of structural components of the embodiment;

FIGS. 13 and 14 are transmission characteristic curves of the members used in the embodiment;

DESCRIPTION OF THE PREFERRED EMBODIMENTS

Figure 17:
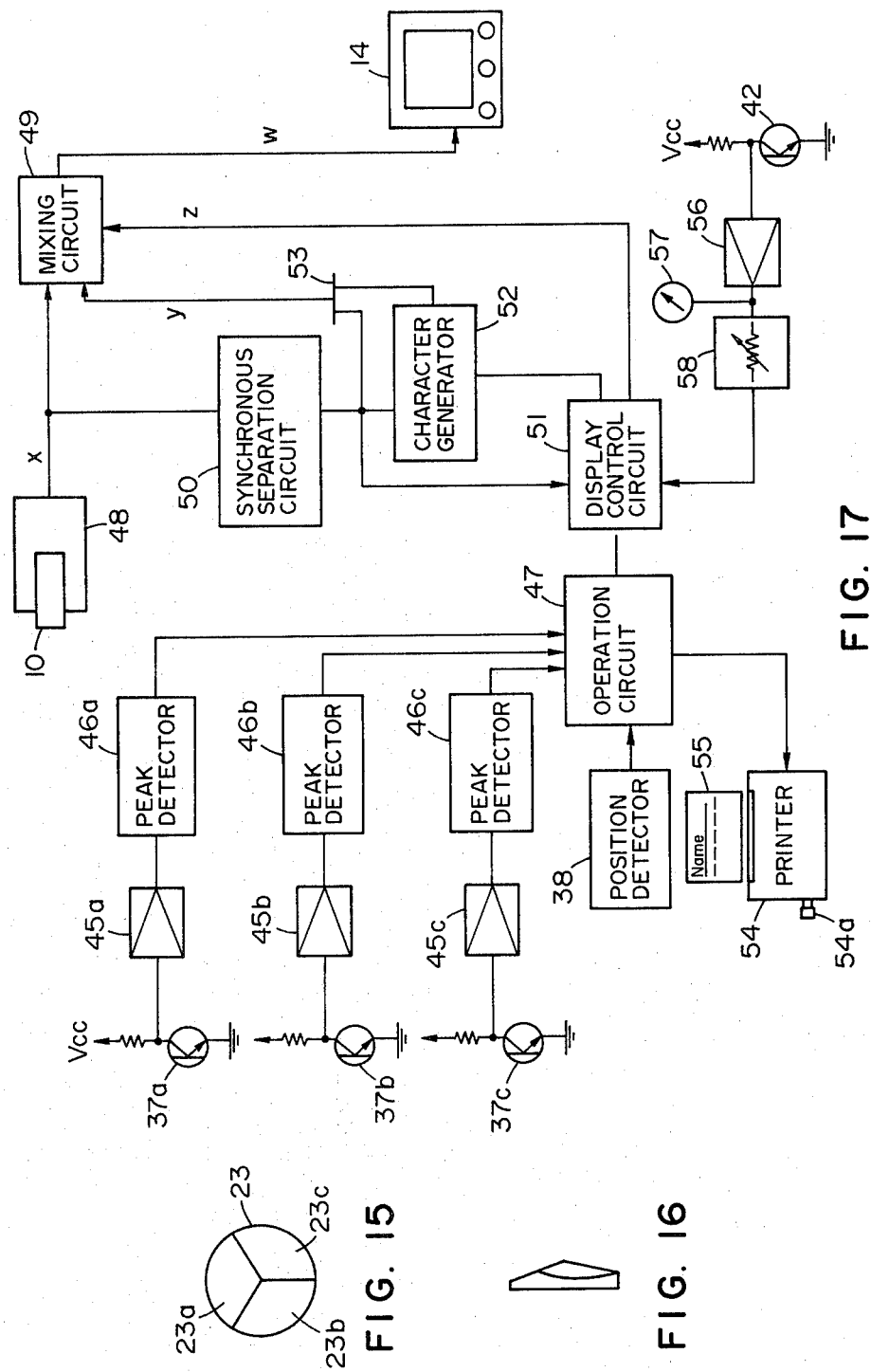
FIG. 17 shows an electric circuit used in the embodiment.

In FIG. 1, an eye to be examined is designated by E, the fundus of the eye, namely the retina of the eye by Ef, the pupil thereof by Ep and the cornea of the eye by Ec. Designated by 1 is a fixation object which may be a flickering light source, a symbol or a picture disposed spaced from the eye. 2 is a dichroic mirror having a particular transmittivity characteristic curve T as shown in FIG. 13. The dichroic mirror 2 reflects those rays of light whose wavelength is longer than that of near infrared ray and transmits those rays of light having shorter wavelength than that. Since the dichroic mirror 2 is arranged slanted relative to the view line of the eye E gazing at the fixation object 1, the person whose eye is examined can see the fixation object 1 through the mirror 2. The size and structure of the mirror 2 are so determined that during measurement the examinee can see the fixation object through the mirror with his two eyes. As to the design of such dichroic mirror reference is made to Japanese patent application No. 88865/1978.

Designated by 3 is an objective lens disposed in such manner that the optical axis of the lens may coincide with the view line of the eye E divided by the dichroic mirror 2. The mirror 2 and objective lens 3 constitute together an objective optical system. Designated by 4 is a part of the apparatus serving to project and detect a test pattern for measurement. A detailed description of this part 4 will be made later with reference to FIG. 6.

5 is a second dichroic mirror having a particular transmittivity characteristic curve T as shown in FIG. 14. More particularly, the second dichroic mirror 5 reflects infrared rays and transmits those rays of light whose wavelength is shorter than that of infrared. 6 is a beam splitter and 7 is an aperture lens. As shown in FIG. 2, the lens 7 has a hole 7a aligned with the optical axis. Function of the hole 7a will be described later.

8 is a target plate having therein a target mark 8a (FIG. 3). 9 is a relay lens, 10 is a pickup tube or an array of pickup elements such as vidicon and 11 is a red light emission diode for illuminating the eye to be examined. The diode is arranged at the outside of the casing of the apparatus.

The conjugated relation of the above described various members is suggested by the broken lines in the drawing. The front part of the eye E, for example, the surface of cornea Ec and the target plate 8 are arranged conjugated relative to the reflection surface of the mirror 2, objective lens 3 and aperture lens 7 whereas the target plate 8 and the light receiving surface of the image pickup tube 10 are conjugated relative to the relay lens 9. With this arrangement, the image pickup tube 10 picks up the image of the target mark and the image of the front part of the eye overlapping each other.

12 is a diode which emits light of longer wavelength than near infrared. 13 is a screen plate having therein a pin hole 13a serving as an alignment mark. While in the shown embodiment the screen plate 13 has only one pin hole on the optical axis, a plural number of such pin holes may be formed symmetrically relative to the optical axis. The position of the screen plate 13 is determined in the following manner:

When the eye to be examined and the objective optical system are in a correct relative position and when the cornea is regarded as a convex mirror, the beam of light emerging from the pin hole 13a can be reflected upon the reflecting surface of the beam splitter 6 to the first dichroic mirror 2 passing through the second dichroic mirror 5 and the objective lens 3 which converges the reflected beam. The first dichroic mirror 2 reflects the beam to the cornea Ec. Upon the cornea, the beam of light is mirror reflected to the first dichroic mirror 2 which reflects again the beam to the objective lens 3. The objective lens again converges the beam of light. The convergent beam passes through the second dichroic mirror 5, beam splitter 6 and hole 7a of the aperture lens 7. Finally, an image of the pin hole 13a is formed on the target plate. In this manner, the pin hole 13a is positioned conjugated with the focal point of the convex mirror, that is, the cornea (which lies at the middle between the cornea vertex and the curvature center of the cornea surface) relative to the beam splitter 6, objective lens 3 and dichroic mirror 2. The target plate 8 is positioned in the rear focal plane of the objective lens 3. With this arrangement, light reflected upon the cornea is converted into parallel rays and imaged on the target plate 8 through the objective lens 3. Also, on the target plate there is formed an image of the front part of the eye (Ec) by a composite refractive power of the objective lens 3 and the aperture lens 7.

The manner of operation of the above described apparatus is as follows:

When diodes 11 and 12 are energized, infrared/near infrared rays are emitted therefrom. The infrared/near infrared rays emitted from the diode 11 illuminate the front part of the eye to be examined and the rays diffuse-reflected thereupon are directed to the first dichroic mirror 2. The rays reflected upon the surface of the mirror 2 enter the objective lens 3 which converges the rays into a convergent beam. Only the near infrared component of the convergent beam passes through the second dichroic mirror 5 and then passes through the beam splitter 6. This beam of light is once imaged on the target plate owing to the refractive power of the aperture lens 7 and then imaged on the light receiving surface of the image pickup tube 10 through the relay lens 9.

On the other hand, the infrared/near infrared rays emitted from the diode 12 enter the beam splitter 6 which allows only the near infrared component to pass through it. The near infrared component passed through the beam splitter is directed to the eye under examination. However, since the dichroic mirror 2 reflects near infrared rays, an image of the pin hole 13a is formed on the light receiving surface of the image pickup tube 10 by the optical action described above.

FIG. 4 shows a television image receiving device 14 which is electrically connected with a television camera including the above mentioned image pickup tube 10. On the picture screen of a television tube such as Braun tube of the image receiving device 14 there are displayed an image of the front part of the examined eye, an image of target mark 8a' and an image of alignment mark 13a'. In the case shown in FIG. 4, the pupil of the examined eye and the target mark 8a' appearing on the television screen are out of alignment and the alignment mark image 13a' appears obscured on the screen. This gives to the examiner a notice that the eye to be examined and the objective optical system of the apparatus are out of alignment to each other and that the distance between the eye and the objective optical system should be adjusted more correctly. So, the examiner or operator moves the apparatus vertically and horizontally as well as backward and forward so as to adjust the apparatus to the position indicated in FIG. 5.

In FIG. 5, the target mark 8a' and the pupil of the examined eye appearing on the television screen are concentrically aligned to each other and the alignment mark 13a' lies in the center of the target mark 8a'. The image of the alignment mark appears clearly and sharply on the screen.

In this connection, one may think that a target mark is dispensable so long as an alignment mark is used. However, the use of a target mark has a particular advantage. Generally, such measuring system using mirror reflection has extremely high sensitivity and therefore it is difficult to make the alignment mark appear at once on the screen of the monitor television set without any rough alignment prior to the necessary fine adjustment. In this sense, the combination of target mark and alignment mark makes the alignment work very easy.

Now, the measuring part of the apparatus is described in detail with reference to FIG. 6.

In the shown embodiment, measurement is carried out by projecting three sets of test patterns corresponding to three longitudinal lines respectively. At first, the reason why three longitudinal lines have been selected will be explained.

Assuming that the eye to be examined has some astigmatism and that the diopter of the astigmatic eye in the longitudinal direction changes in a manner of a sine wave, then the diopter is a function of the angle of longitude and can be represented by the following formula (1):

$$D = A \sin(2\theta + \alpha) + B \qquad (1)$$

wherein, variables D and $\theta$ are diopter and angle in the longitudinal direction respectively and constants A, B and $\alpha$ are astigmatism, average diopter and direction of astigmatic axis respectively.

The above formula (1) contains three unknown values. Therefore, the aimed values of astigmatism, average diopter and astigmatic axis can be obtained by obtaining measured values in at least three longitudinal directions and applying the measured values to the formula (1). Of course, the number of longitudinal directions to be selected for measurement is never limited only to three. By increasing the number of longitudinal directions for measurement and averaging the values given by first measurement using first combination of three directions and those by second measurement using second combination, accuracy of measurement can be improved further.

Figure 15:
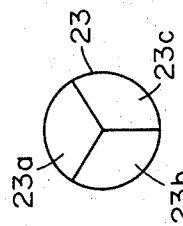
FIG. 15 is a plan view of one component used in the embodiment.
Figure 16:
FIG. 16 is a side view thereof.

In FIG. 6, the reference numeral 20 designates an infrared light emitting diode and 21 is an aperture diaphragm plate having an opening 21a as shown in FIG. 9. The diaphragm plate functions to separate three beams. 22 is a condenser lens and 23 is a declination prism. The declination prism 23 has a particular shape as shown, in plan view, in FIG. 15 and, in side view, in FIG. 16. The function of the prism 23 is to deflect the beams of light incident upon its respective surfaces outwardly.

24 is a three beam slit plate having therein three slits 24a, 24b, 24c extending normally to longitudes and disposed at the relative angle position of 120° to each other. These slits forms a test pattern. The declination prism 23 is disposed in the vicinity of the three beam slit plate 24 at the upperstream or at the downstream side thereof. 25 is a relay lens and 26 is a three hole plate. The plate 26 has three openings 26a 26b, 26c arranged corresponding to three longitudinal lines respectively as shown in FIG. 7. 27 is another relay lens which is movable in the direction of the optical axis together with the members 25 and 26 as one unit.

28 is a relay lens and 29 is an aperture mirror. As shown in FIG. 8, the mirror 29 has three openings 29a, 29b, 29c arranged corresponding to three longitudinal lines respectively.

Also, 30 and 32 are relay lenses and 33 is a diaphragm plate having an opening 33a as shown in FIG. 12. Designated by 34 is a relay lens which is movable in the direction of the optical axis together with the members 32 and 33 as one unit. The composite refractive power of the lenses 32 and 34 is equal to that of the lenses 25 and 27. The first unit (25, 26, 27) is connected with the second unit (32, 33, 34) and the two units are moved together in one direction by driving means not shown once for every measurement.

Designated by 35 is a three beam slit plate the structure of which is the same as that shown in FIG. 10. 36a, 36b and 36c are light guides each of which may be a bundle of optical fibers or a light transmission rod made of acrylic resin. One end of each the light guide is connected to the corresponding one of the three slits formed in the three beam slit plate 35 and the other end is connected to a photoelement such as phototransistor.

With the above described optical arrangement, the three beam slit plates 24 and 35 can maintain their conjugate relation with the point P relative to the relay members.

38 is position detection means having a measuring device such as encoder. The detection means continuously detects the position on the axis of the above described movable unit. While in the shown embodiment the relay lenses are moved as a movable unit, it is also possible to move the three beam slit plate, instead of moving the relay lenses, together with the illumination part and photometry part in the axial direction.

The manner of operation of the above described measuring part is described hereinafter with reference to FIG. 6 in which the beam of light shown for indicating the conjugate relation should be considered as such one which is emitted from any one of three slits on the three beam slit plate.

Upon lighting of the light emitting diode 20, the aperture diaphragm plate 21 is illuminated by infrared light emitted from the diode. A beam of light coming from the opening 21a is concentrated on the three beam slit plate 24 through the condenser lens 22. The beam is separated into three beams under the action of the three slits 24a, 24b, 24c and the action of the declination prism 23 having three separation surfaces 23a, 23b, 23c. The separate three beams are subjected to the converging action of the relay lens 25 and the beams enter the relay lens 27 while the beams being prevented from interference with each other by the respective openings 26a, 26b, 26c in the three hole plate 26. After passing through the relay lens 27, the beams once form images and then diverge. The diverging beams are converged by the relay 28 and the converging beams pass through the openings 29a, 29b, 29c in the aperture mirror 29 respectively. After being reflected by the second dichroic mirror 5, these beams again form images and then begin to diverge. The diverging beams are converged by the objective lens 3 and diverged by the first dichroic mirror 2. Then, these beams form an image of the test pattern on a concave surface containing the point P and normal to the optical axis.

When the point P lies just in the fundus Ef, the beams diffuse-reflected upon the fundus of the eye emerge from the eye and go back along the optical path which they have once come along. Thus, the beams are reflected upon the dichroic mirror 2 and form once images through the objective lens 3. Then, the beams are reflected by the second dichroic mirror 5 and by the mirror surface of the aperture mirror 29 to the relay lens 30 which focus the beams on a plane behind the beam splitter 31. After passing through the relay lens 32, diaphragm plate 33 and relay lens 34, the beams form images on the three beam slit plate 35. The three beams which have passed through the slits 35a, 35b, 35c respectively enter the photo elements 37a, 37b, 37c through the light guides 36a, 36b, 36c. Since, as mentioned above, the point P lies just in the fundus in this case, the respective images of the test pattern forming slits provided in the three beam slit plate 24 are exactly coincident with the three slits on the detection three beam slit plate. Therefore, the images of slits then formed become sharp and clear and the quantity of light received by the photo elements becomes maximum.

However, if the point P is not in the fundus Ef but in a position before or after the fundus, then no sharp image of the test pattern is obtained. In this case, the test pattern image formed on the detection three beam slit plate 35 gets not only obscured but also deviated in the longitudinal direction. This results in reduction of quantity of light received by the photo elements. The deviation of the position of image is caused by the fact that the image is formed by off-axis rays.

With the start of measurement, the combined movable units (25, 26, 27; 32, 33, 34) are moved in the direction of the arrow. The quantity of light incident upon the photo elements 37a, 37b, 37c gradually increase with the movement of the movable units. However, when there is astigmatism in the tested eye, it never occurs that all of the three photo elements detect peak values at the same time. They reach the peak value one by one.

An example of electric circuit useful for the measuring apparatus is shown in FIG. 17. In this example, as photo elements, there are used photo transistors, 37a, 37b and 37c.

Output signals from the photo transistors 37a, 37b, 37c are amplified in the amplifiers 45a, 45b, 45c and then introduced into peak detectors 46a, 46b, 46c respectively to detect the peak value. Vcc indicates connection with a constant voltage power source.

During measurement, the position detector 38 continues to put a position detection signal into the operation circuit 47. By applying to the above formula (1) three sets of position signals appearing at the time point when peak value is detected, the aimed information can be obtained. For the equation of $D = A \sin(2\theta + \alpha) + B$, the diopter (refractive power) D is determined by the position of the movable unit and the angle of longitude $\theta$ is predetermined. Therefore, the average diopter (SPHERE) A, astigmatism (CYLINDER) B and astigmatic axis (AXIS) $\alpha$ are obtainable by calculation.

Figure 18:
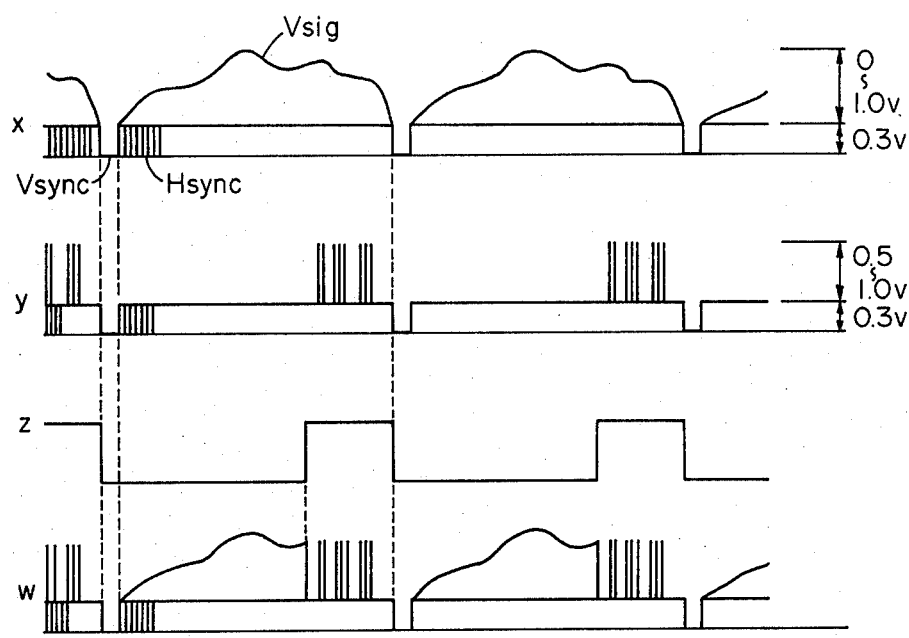
FIG. 18 shows wave forms of electric signals in the circuit.

On the other hand, outputs (x) from the television camera 48 constitute video signals corresponding to the image of the front part of the examined eye and the images of target and alignment marks given by the above described image pick-up tube 10. As shown in FIG. 18, a video signal x is composed of three components, video signal Vsig, vertical synchronizing signal Vsync and horizontal synchronizing signal Hsync. This signal is put into the television receiver 14 through a mixing circuit 49 (FIG. 17). At this time, video signal x is separated into video signal and synchronizing signals by a synchronous separation circuit 50. Data computed in the operation circuit 47 come out as digital signals from display control circuit 51 and character generator 52. OR gate 53 compounds the digital signals into a character signal y. The character signal y constitutes one input signal to the mixing circuit 49 and another input signal to the latter is video signal x. These two input signals x and y are mixed by a change-over signal z coming from the display control circuit 51 and form a new mixed signal w. The signal w is introduced into the television receiver 14 and displayed on the television screen as an image of the front part of the examined eye at the upper area of the screen as well as measured data at the lower area as illustrated in FIG. 5. Arrangement of numerals and characters on the screen can be selected optionally. Technique for displaying various symbols such as numerals and characters on a television screen plate is well known to those skilled in the art by teachings in U.S. Pat. No. 3,345,458.

FIG. 18 shows a typical example of wave form of the above described signals wherein abscissa is time and orginate is voltage.

Generally speaking, video signal Vsig is at the level of from 0 to 1.0 V whereas synchronizing signals Vsync and Hsync are at the level of from 0.2 to 0.3 V. When the character signal y is at the video level of from 0.5 to 1.0 V, there are displayed on a Braun tube characters in white on black background.

As mixing circuit 49 there may be used an integrated circuit commercially available such as MC 1545 (Motoroller Company). Also, the mixing circuit 49 may be composed of discrete elements.

In FIG. 17, the reference numeral 54 designates a printer and 55 is a customer card. After insertion of the card into the printer and confirming the result of measurement on the television 14, the operator releases a release button 54a. Thereby date of measurement and the result of measurement are printed on the blank of the card.

Now, description is made as to checking operation of photometric conditions with reference to FIG. 6.

In FIG. 6, an imaging lens is designated by 40, an aperture diaphragm plate by 41 and a photo element by 42. The photo element 42 is disposed close to the aperture diaphragm plate. The aperture diaphragm plate 41 is disposed conjugate with the pupil Ep of the eye to be examined relative to imaging lens 40, relay lens 30, aperture mirror 29, second dichroic mirror 5, objective lens 3 and first dichroic mirror 2. Also, the diameter of diaphragm aperture is so measured as to contain three beams whose images formed on the pupil pass through the pupil.

With this arrangement, among three beams reflected upon the fundus of the eye such beam can enter the photo element 42 which is divided by the beam splitter 31. By measuring the quantity of light incident upon the photo element the operator can know the difference in fundus reflection between individuals, which is useful for adjustment of amplification level of amplifiers 45a, 45b, 45c. Furthermore, checking as to whether or not light reflected upon the cornea is present or as to whether there is any external disturbance (by meter 57) can be done making use of detected light on the photo element 42. Also, in the shown embodiment, to detect winking of the examined eye during measurement the signal from the photo element 42 is amplified by an amplifier 46 and compared with a predetermined reference signal in a comparator 58. When the result of comparison indicates occurrence of wink, it is displayed on the television tube 14. Since the measuring light is reflected upon eyelid of the examined eye upon the time of winking, the quantity of light incident upon the photo element 42 substantially increases at the time of winking. This is used to detect occurrence of wink of eye during measurement. Display of winking on the television tube prevents the operator from failing to notice the wink.

Various modifications can be made in the shown embodiment. For example, in parallel with the target plate shown in FIG. 1 there may be provided the display surface of a display device such as liquid crystal display for displaying data coming from the operation circuit so that both of the target plate and the data displaying surface may be photographed at the same time. But, the use of electric processing circuit of television has an advantage that in addition to numerals any character signal can be displayed as desired.

The present invention has many effects and advantages.

Firstly, according to the invention, the examiner can observe the eye to be examined immediately before and after measurement. For prior art apparatus, measurement is carried out on the assumption that so long as the person under examination is gazing at the fixation object his view line is in a normal position. However, there are often such cases where the eye has a slight strabismus and/or where the view line is somewhat deviated from the normal position due to high tension of the person gazing at the fixation object forcedly. In such case, the result of measurement includes some error. If spectacles are prepared for him based upon such result of measurement, a time—and labour consuming correction will be required. According to the present invention the examiner can give the person gazing at the fixation object an advice to prevent such error while observing the monitoring screen. Thus, an essential improvement in measurement accuracy is attainable.

Secondly, the measuring apparatus enables the examiner to observe the examined eye during measurment. Therefore, during measurement the examiner can check as to whether or not the person under examination is correctly gazing at the fixation object and whether or not the person winks his eyes. This contributes to a further improvement of measuring accuracy.

Thirdly, with the measuring apparatus according to the invention the examiner can accomplish a centralized observation very easily because the result of measurement is displayed on a monitor-display screen. The examiner can observe the examined eye while comparing the state of the eye during measurement with the result of measurement. Therefore, the examiner can easily and promptly make a decision as to whether one more measurement should be carried out.

It is another advantage of the invention that setting ability can be improved with the alignment device according to the invention.

As shown in the embodiment, according to the invention, the measuring system and the observation system can be separated from each other (for example, lights of different wavelengths are used). This makes it possible to continue observing during measurement without putting any adverse effect on the measuring system.

Also, as in the embodiment, the measuring system and the observation system use a common objective optical system. This makes it possible to observe the examined eye in a front view through the observation system and therefore the examiner can easily perceive abnormal viewing manner of the eye under examination if any. On the other hand, the use of a common objective optical system has an effect to reduce the number of component members necessary for the apparatus.

Time required for one measurement with the apparatus according to the invention is very short and therefore remeasurement can be carried out very easily and conveniently. Since measuring time is very short, there is no trouble of the condition of refractive power of the examined eye being changed during a measurement.

While the invention has been particularly shown and described with reference to preferred embodiments thereof, it will be understood by those skilled in the art that the foregoing and other changes in form and details can be made therein without departing from the spirit and scope of the invention.

What we claim is:

1. An apparatus for automatically measuring the refractive power of an eye, comprising:
   a diopter measuring system for directing radiant energy to the fundus of an eye to be examined, detecting the focus of the radiant energy reflected upon the fundus of the eye and operating on the signal stream of focus detection;
   means for converting said signal stream into a video signal which forms a character pattern;
   a video camera for photographing the front part of the eye; and
   a video display device electrically connected with said converting means and with said video camera for receiving said video signal and displaying said character pattern and for displaying the front part of the eye.

2. A measuring apparatus according to claim 1, which further comprises mark projection means for projecting a marking beam which is reflected upon the front part of the eye to be examined and forms an image on the photosensitive plane of said video camera.

3. A measuring apparatus according to claim 1, which further comprises photo detecting means disposed focused at the front part of the eye to be examined, output of said photo detecting means being fed to said converting means after comparison with a predetermined reference value in a comparator circuit.

4. A measuring apparatus according to claim 1, wherein said diopter measuring system comprises target means for generating a pattern of radiant energy, optical means for projecting said pattern and making said pattern focused at the fundus of the eye to be examined, sensing means for detecting said pattern passed through said optical means, a position detector connected with said optical means and operation means for performing operation on the output coming from said sensing means and position detector in accordance with a predetermined program.

5. A measuring apparatus according to claim 4, wherein said pattern of radiant energy is composed of sub-patterns corresponding to at least three longitudinal lines respectively.

6. A measuring apparatus according to claim 4, wherein said sending means includes photo cells fixed corresponding to at least three longitudinal lines respectively.

7. An automatic eye-refractometer comprising:
   a fixation object for fixing the view line of the eye to be examined;
   diopter measuring means for directing radiant energy to the fundus of the eye including objective optical means through which the radiant energy passes, and for detecting the focus of the radiant energy reflected upon the fundus of the eye and operating on the signal stream of focus detection;
   a casing for accommodating said diopter measuring means;
   a beam splitter, projected out of said casing, for reflecting the radiant energy toward the eye from said objective optical means and for showing said fixation object;
   means for converting said signal stream into a video signal which forms a character pattern;
   video photographing means for photographing the front part of the eye through said objective optical means; and
   video display means electrically connected with said converting means and said video photographing means.

* * * * *

UNITED STATES PATENT AND TRADEMARK OFFICE
CERTIFICATE OF CORRECTION

PATENT NO. : 4,372,655  Page 1 of 2
DATED : February 8, 1983
INVENTOR(S) : ISAO MATSUMURA, ET AL.

It is certified that error appears in the above-identified patent and that said Letters Patent is hereby corrected as shown below:

Column 1

Line 25, change "changed" to --change--.

Column 5

Line 40, change "forms" to --form--.

Line 67, change "One end of each the light guide" to --One end of each of the light guides--.

Column 7

Line 68, change "orginate" to --ordinate--.

Column 8

Lines 9 and 10, change "Moto-roller Company" to --Motorola Company--.

UNITED STATES PATENT AND TRADEMARK OFFICE
CERTIFICATE OF CORRECTION

PATENT NO. : 4,372,655

DATED : February 8, 1983

INVENTOR(S) : ISAO MATSUMURA, ET AL.

It is certified that error appears in the above-identified patent and that said Letters Patent is hereby corrected as shown below:

Column 9

Line 20, change "measurment" to --measurement--.

Line 32, change "of measurement" to --of the measurement--.

Line 44, change "as in the embodiment" to --as shown in the embodiment--.

Signed and Sealed this

Thirtieth Day of August 1983

[SEAL]

Attest:

GERALD J. MOSSINGHOFF

Attesting Officer

Commissioner of Patents and Trademarks